United States Patent
Hahn et al.

(10) Patent No.: US 8,183,229 B2
(45) Date of Patent: May 22, 2012

(54) BONE FILLING COMPLEX AND METHOD FOR FABRICATING THE SAME

(75) Inventors: Sei Kwang Hahn, Pohang-si (KR); Eun Ju Oh, Busan (KR); Jung Kyu Park, Daejeon (KR); Kwang Bum Park, Daegu (KR); Kyoung Ho Ryoo, Gwangju (KR); Seok Kyu Choi, Busan (KR); Dong Jun Yang, Daegu (KR); Hyun Wook An, Gyeongsan-si (KR)

(73) Assignees: Megagen Implant Co., Ltd. (KR); Pohang University of Science and Technology Dept. of Advanced Materials Science & Engineering (KR)

( * ) Notice: Subject to any disclaimer, the term of this patent is extended or adjusted under 35 U.S.C. 154(b) by 436 days.

(21) Appl. No.: 12/438,628

(22) PCT Filed: Aug. 27, 2007

(86) PCT No.: PCT/KR2007/004110
§ 371 (c)(1),
(2), (4) Date: Feb. 24, 2009

(87) PCT Pub. No.: WO2008/026858
PCT Pub. Date: Mar. 6, 2008

(65) Prior Publication Data
US 2010/0249059 A1    Sep. 30, 2010

(30) Foreign Application Priority Data

Aug. 31, 2006  (KR) .................. 10-2006-0083417

(51) Int. Cl.
*A61K 31/70*  (2006.01)
*C07H 5/04*   (2006.01)
(52) U.S. Cl. .................. 514/54; 536/55.1; 536/55.2
(58) Field of Classification Search ............. 536/55.1, 536/55.2
See application file for complete search history.

(56) References Cited

U.S. PATENT DOCUMENTS

| | | |
|---|---|---|
| 4,970,298 A | 11/1990 | Silver et al. |
| 5,015,677 A | 5/1991 | Benedict et al. |
| 5,752,974 A | 5/1998 | Rhee et al. |
| 5,874,417 A | 2/1999 | Prestwich et al. |

OTHER PUBLICATIONS

International Search Report for PCT/KR2007/004110, dated Dec. 18, 2007.
Written Opinion for PCT/KR2007/004110, dated Dec. 18, 2007.

*Primary Examiner* — Elli Peselev
(74) *Attorney, Agent, or Firm* — Cantor Colburn LLP (57) ABSTRACT

Provided is a bone filling complex and method of preparing the same. The bone filling complex includes a matrix including a hydrogel-type hyaluronic acid derivative; and a bone derivative filling the matrix For example, the bone filling complex can be used to regenerate an injured alveolar bone.

29 Claims, 4 Drawing Sheets

BONE FILLING COMPLEX AND METHOD FOR FABRICATING THE SAME

TECHNICAL FIELD

The present invention is directed to a bone filling complex and a method of fabricating the same, and more specifically, to a bone filling complex including a hyaluronic acid derivative and a method of fabricating the same.

BACKGROUND ART

In general, when a bone is injured by a trauma or osteoporosis, the injured portion is filled with another bone by synostosis. The synostosis is categorized into an autogenous bone grafting method in which bone grafts are transplanted from one area of an individual's body to another area of the individual's body and a heterogenous bone grafting method in which a bone of an animal is chemically treated and the chemically treated bone is transplanted.

The autogenous bone grafting method has such disadvantages that the amount of bone to be collected is small and complication may occur surrounding the transplanted portion. The heterogenous bone grafting method has such disadvantages that immunological reaction may occur and synostosis can be delayed. For example, use of a cow-derived heterogenous bone graft may cause a mad cow disease.

Recently, many bone fillers which replace an autogenous bone and a hetero bone have been developed. For example, a calcium phosphate-based compound which forms a bone or teeth can act as a bone filler. However, when an injured portion of a bone is cured with the bone filler, adhesion may occur in which excess fibrous tissues are generated and abnormal conjugations between adjacent tissues occur. Although some of the abnormal conjugations decompose spontaneously, but most of them remain and sequela is caused even after the injury is cured.

Accordingly, there is a need to develop a bone filler that can efficiently regenerate a bone and prevent adhesion at the injured portion of a bone.

DETAILED DESCRIPTION OF THE INVENTION

Technical Problem

The present invention provides a bone filling complex having an excellent bone regeneration property and an excellent adhesion prevention property.

The present invention also provides a method of preparing a bone filling complex having an excellent bone regeneration property and an excellent adhesion prevention property.

ADVANTAGEOUS EFFECTS

A bone filling complex according to the present invention includes a hyaluronic acid derivative-containing matrix and a bone alternative which fills the matrix, and thus adhesion can be prevented. The bone filling complex also has an excellent bone regeneration property and thus, when the bone filling complex is used to an injured portion of an alveolar bone, the alveolar bone can be regenerated.

BEST MODE

According to an embodiment of the present invention, there is provided a bone filling complex including: a matrix including a hydrogel-type hyaluronic acid derivative; and a bone derivative which fills the matrix.

The hydrogel-type hyaluronic acid derivative can be obtained by reacting a hyaluronic acid with suberate. The suberate can be bis(sulfosuccinimmidyl)suberate.

The suberate can be bonded to a carbonyl group of the hyaluronic acid through a linker.

The linker includes at least two amino groups, wherein one amino group of the amino groups can be bonded to the carboxylic group of the hyaluronic acid and another amino group of the amino groups can be bonded to a carbonyl group of the suberate.

The matrix includes at least one unit represented by Formula 1:

Formula 1 where $R_1$ and $R_2$ can be respectively a hydrogen atom or $C_{1-6}$ alkyl group; and $R_3$ is a single bond, —$(CH_2)x$—, —$CH_2$—$CH_2$—$(O$—$CH_2$—$CH_2)x$—, or —$NHCO$—$(CH_2)y$—$CONH$— where x is an integer of from 1 to 10 and y is an integer of from 0 to 10. Each of $R_1$ and $R_2$ can be hydrogen atom and $R_3$ can be —$NHCO$—$(CH_2)y$—$CONH$—.

The hydrogel-type hyaluronic acid derivative can be obtained by reacting a hyaluronic acid to which a methacrylic anhydride is introduced with a dithiol-based crosslinker.

The methacrylic anhydride can be bonded to a carboxylic group of the hyaluronic acid through a linker.

The linker includes at least two amino groups, wherein one amino group of the amino groups can be bonded to the carboxylic group of the hyaluronic acid and another amino group of the amino groups can be bonded to a carbonyl group of the methacrylic anhydride.

The dithiol-based crosslinker can be a peptide which has cysteine at its opposite ends and an arginin-glycine-aspartic acid sequence interposed between the ends.

The matrix includes at least one unit represented by Formula 2.

The matrix can have a network structure.

The bone derivative can be a calcium phosphate-based compound.

The bone filling complex can be formulated into blocks, granules, or an injectable form.

According to another aspect of the present invention, there is provided a method of preparing a bone filling complex, the method including: forming a matrix comprising a hydrogel-type hyaluronic acid derivative; and filling the matrix with a bone derivative.

The forming of a matrix includes reacting a hyaluronic acid with suberate. The suberate can be bis(sulfosuccinimmidyl) suberate.

The suberate can be bonded to a carbonyl group of the hyaluronic acid through a linker.

The linker includes at least two amino groups, wherein one amino group of the amino groups can be bonded to the carboxylic group of the hyaluronic acid and another amino group of the amino groups can be bonded to a carbonyl group of the suberate.

The matrix includes at least one unit represented by Formula 1:

Formula 2 where $R_1$ and $R_2$ can be respectively a hydrogen atom or $C_{1-6}$ alkyl group; $R_3$ is a single bond, —$(CH_2)x$—, —$CH_2$—$CH_2$—$(O$—$CH_2$—$CH_2)x$—, or —$NHCO$—$(CH_2)y$—$CONH$— where x is an integer of from 1 to 10 and y is an integer of from 0 to 10; C is cysteine; R denotes arginin; G denotes glycine; D denotes aspartic acid; and (—S—) denotes a sulfur derived from a mercapto group contained in cysteine. Each of $R_1$ and $R_2$ can be hydrogen atom and $R_3$ can be —$NHCO$—$(CH_2)y$—$CONH$—.

Formula 1 where $R_1$ and $R_2$ can be respectively a hydrogen atom or $C_{1-6}$ alkyl group; and $R_3$ is a single bond, —$(CH_2)x$—, —$CH_2$—$CH_2$—$(O$—$CH_2$—$CH_2)x$—, or —NHCO—$(CH_2)y$—CONH— where x is an integer of from 1 to 10 and y is an integer of from 0 to 10. Each of $R_1$ and $R_2$ can be hydrogen atom and $R_3$ can be —NHCO—$(CH_2)y$—CONH—.

The linker can be bonded to the carboxylic group of the hyaluronic acid in a solution comprising at least one organic solvent in an amount ranging from 0 to 60 vol %. The organic solvent can be ethanol.

The forming of the matrix includes: introducing methacrylic anhydride to a hyaluronic acid; and reacting the hyaluronic acid to which the methacrylic anhydride can be introduced with a dithiol-based crosslinker.

The methacrylic anhydride can be bonded to a carboxylic group of the hyaluronic acid through a linker.

The linker includes at least two amino groups, wherein one amino group of the amino groups can be bonded to the carboxylic group of the hyaluronic acid and another amino group of the amino groups can be bonded to a carbonyl group of the methacrylic anhydride.

The dithiol-based crosslinker can be a peptide which has cysteine at its opposite ends and an arginin-glycine-aspartic acid sequence interposed between the ends.

The matrix includes at least one unit represented by Formula 2:

Formula 2 where $R_1$ and $R_2$ can be respectively a hydrogen atom or $C_{1-6}$ alkyl group; $R_3$ is a single bond, —$(CH_2)x$—, —$CH_2$—$CH_2$—$(O$—$CH_2$—$CH_2)x$—, or —NHCO—$(CH_2)y$—CONH— where x is an integer of from 1 to 10 and y is an integer of from 0 to 10; C is cysteine; R denotes arginin; G denotes glycine; D denotes aspartic acid; and (—S—) denotes a sulfur derived from a mercapto group contained in cysteine. Each of $R_1$ and $R_2$ can be hydrogen atom and $R_3$ can be —NHCO—$(CH_2)y$—CONH—.

The linker can be bonded to the carboxylic group of the hyaluronic acid in a solution comprising at least one organic solvent in an amount ranging from 0 to 60 vol %. The organic solvent can be ethanol.

The bone derivative can be a calcium phosphate-based compound.

The forming of the matrix and the filling with the bone derivative are substantially performed in situ.

MODE OF THE INVENTION

Embodiments of the present invention are described in detail in the detailed description and the accompanying drawings. The advantages and features of the present invention and a method of realizing the present invention will be clarified with reference to embodiments which will now be described more fully with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. The present invention is defined by definitions recited in the claims only. In the specification, like reference numerals in the drawings denote like elements.

A bone filling complex according to an embodiment of the present invention will now be described in detail.

The bone filling complex includes a matrix including a hydrogel-type hyaluronic acid derivative and a bone derivative which fills the matrix.

The matrix of the bone filling complex will now be described in detail.

The matrix acts as a physical barrier which separates tissues from each other when the bone filling complex is injected into a body and regenerates a bone tissue. The matrix covers or surrounds a lesion or injury which is to be adhesive, and after a predetermined period of time, decomposes and is substituted into a regenerated bone tissue. The matrix includes a hydrogel-type hyaluronic acid derivative. The matrix can have, for example, a network structure.

Specifically, the matrix can be obtained by reacting a hyaluronic acid with suberate. The suberate which is to react with the hyaluronic acid can be Bis[sulfosuccinimmidyl]suberate.

The hyaluronic acid is, as illustrated in Formula 3, is a type of a glycosaminoglycan composed of a disaccharide unit in which D-glucuronic acid is linked to N-acetylglucosamine via a β (1→3) glycosidic bond. Every species has the same chemical and physical structure of the hyaluronic acid, and human also has a metabolic system with respect to the hyaluronic acid. The hyaluronic acid is a most stable biomaterial in terms of immunity and toxicity. The hyaluronic acid can be mass-produced by, for example, fermenting a microorganism. When the hyaluroic acid is mass-produced by fermenting a microorganism, virus contamination and allergy reaction may not occur and a predetermined degree of quality can be maintained constant.

Formula 3

In the present specification, the terminology "hyaluronic acid" refers to, in addition to a hyaluronic acid itself, a salt thereof. That is, in the present specification, the "hyaluronic acid" can be a hyaluronic acid, a hyaluronic acid salt, or a mixture of the hyaluronic acid and the hyaluronic acid salt. Examples of the hyaluronic acid salt include an inorganic salt, such as sodium hyaluronic acid, magnecium hyaluronic acid, zinc hyaluronic acid, or cobalt hyaluronic acid; and an organic salt, such as tetrabutylammonium hyaluronic acid. In some cases, the hyaluronic acid salt can be a combination of these. In the present invention, the molecular weight of the hyaluronic acid is not limited. For example, the molecular weight of the hyaluronic acid may be in the range from 100,000 to 10,000,000.

In the matrix, the hyaluronic acid is chemically covalently bonded to suberate. Accordingly, when the hyaluronic acid derivative in which the hyaluronic acid is bonded to suberate is administered in vivo, the hyaluronic acid is not separated from suberate even when the concentration of the salt changes or the pH changes.

The hyaluronic acid can be bonded to suberate through a linker. The linker is bonded to a carbonyl group of suberate and then can be introduced to the hyaluronic acid. The linker regulates the decomposition speed of the hyaluronic acid derivative in vivo. The hyaluronic acid derivative is decomposed by a hyaluronidase which is an enzyme for decomposing a hyaluronic acid present in vivo, in which the hyaluronidase can recognize the hyaluronic acid through a carboxylic group of the hyaluronic acid. Accordingly, the decomposition speed at which the hyaluronic acid derivative is decomposed by the hyaluronidase can be regulated by controlling the number of exposed carboxylic groups by binding the inker to a carboxylic group of the hyaluronic acid. For example, as the linker is more introduced to the hyaluronic acid, the decomposition speed of the hyaluronic acid derivative in vivo is decreased. That is, the decomposition speed of the hyaluronic acid derivative in vivo can be regulated by controlling an introduction rate of the linker to the hyaluronic acid.

The linker can include at least two amino groups. The linker can be a dihydrazide compound including a plurality of amino groups, a diamine compound including a plurality of amino groups, or a hydrazine compound including a plurality of amino groups. The linker can be a diamine compound represented by $H_2N—(CH_2)x—NH_2$ where x is an integer between from 0 to 10 or $H_2NNHCO—(CH_2)—CH_2—(O—CH_2—CH_2)x—NH_2$ where x is an integer between from 0 to 10; a dihydrazide compound represented by $H_2NNHCO—(CH_2)x—CONHNH_2$ where x is an integer between from 0 to 10; or a hydrazine compound represented by $NH(R_1)—NH(R_2)$ where $R_1$ and $R_2$ can be respectively a hydrogen atom or $C_{1-6}$ alkyl group.

The substrate or the linker can be introduced to, for example, a carboxylic group of the hyaluronic acid. Specifically, when the suberate or the linker is introduced to the carboxylic group, the suberate or the linker can be introduced to the hyaluronic acid by forming amid group, hydrazide group, diacylhydrazide group, or carboxylic acid ester group. As for a hyaluronic acid derivative in which suberate or the linker is introduced to a hyaluronic acid by forming a carboxylic acid ester group, the suberate may be decomposed by hydrolysis in an administered solution or in vivo in a relatively short period of time. A linker including amid group or hydrazide group which is slowly hydrolyzed can be used to link suberate to the hyaluronic acid.

The matrix of the bone filling complex according to an embodiment of the present invention described above may include a repeating unit represented by Formula 1:

Formula 1 where $R_1$ and $R_2$ can be respectively a hydrogen atom or $C_{1-6}$ alkyl group; and $R_3$ is a single bond, $—(CH_2)x—$, $—CH_2—CH_2—(O—CH_2—CH_2)x—$, or $—NHCO—(CH_2)y—CONH—$ where x is an integer of from 1 to 10 and y is an integer of from 0 to 10. For example, each of $R_1$ and $R_2$ can be a hydrogen atom and $R_3$ can be $—NHCO—(CH_2)y—CONH—$.

The matrix is filled with the bone derivative. The matrix may have, for example, a network structure. In the network structure, the net is filled with the bone derivative. The bone derivative derives regeneration of a bone tissue at an injured portion of a bone. The bone derivative can be a calcium phosphate-based compound. The bone derivative included in the bone filling complex according to an embodiment of the present invention can be a natural calcium phosphate-based compound or an artificially synthesized calcium phosphate-based compound. The bone derivative can be any material that derives regeneration of a bone tissue.

A method of preparing the bone filling complex which has been described will now be described in detail.

First, a carboxylic group of the hyaluronic acid is actively esterified using a condensing agent selected from the group consisting of N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholinium (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazole-1-yloxy-tris(dimethylamino)phosphoniumhexafluorophosphate (BOP), 1-ethyl-3-(3-dimethylaminopropyl)carbodiimide (EDC), N-hydroxysuccinimide (NHS), and a combination of these.

Then, a linker having a functional group having reactivity with respect to the active ester, such as a linker having a hydrazide group or an amino group, is introduced to the activated carboxylic group. At this time, the linker can be introduced to the carboxylic group of the hyaluronic acid in distilled water or at least one kind of an organic solvent. The organic solvent can be, for example, ethanol. The amount of the organic solvent may be about 60 vol % or less, and specifically about 50 vol %, based on the total amount of the entire solution.

Then, the bone derivative, for example, a calcium phosphate compound is dispersed to the hyaluronic acid solution to which the linker is introduced, and bis(sulfosuccinimidyl)suberate is added thereto. As a result, a bone filling complex in which the matrix having a network structure including the hydrogel-type hyaluronic acid derivative is filled with the bone derivative can be obtained. As described above, formation of the matrix and filling with the bone derivative can be performed substantially in-situ.

The bone filling complex is freeze-dried and formulated into various forms suitable for user's objectives. For example, the bone filling complex can be formulated into blocks, granules, or injectable forms.

The bone filling complex according to an embodiment of the present invention described above can be used as a dental bone filler. That is, an injured portion of an alveolar bone can be filled with the bone filling complex to derive regeneration of the alveolar bone.

A bone filling complex according to another embodiment of the present invention will now be described in detail.

The bone filling complex includes a matrix including a hydrogel-type hyaluronic acid derivative and a bone derivative which fills the matrix.

The hydrogel-type hyaluronic acid derivative included in the matrix is obtained in such a method that a methacrylic anhydride is introduced to a hyaluronic acid and the resultant product is reacted with a dithiol-based crosslinker.

The hyaluronic acid is chemically covalently bonded to methacrylic anhydride. Accordingly, when a hyaluronic acid derivative in which the hyaluronic acid is bonded to methacrylic anhydride is administered in vivo, the hyaluronic acid is not separated from methacrylic anhydride even when the concentration of the salt changes or the pH is changed.

The hyaluronic acid can be bonded to methacrylic anhydride through a linker. The linker can be bonded to a carbonyl group of methacrylic anhydride and then the bonded linker can be introduced to the hyaluronic acid. The linker functions to regulate the decomposition speed of the hyaluronic acid derivative in vivo. The function and kind of the linker are substantially the same as those of the bone filling complex according to the previous embodiment, and thus, will not be described in detail herein.

The methacrylic anhydride or the linker can be introduced to, for example, a carboxylic group of the hyaluronic acid. Specifically, when the methacrylic anhydride or the linker is introduced to the carboxylic group, the methacrylic anhydride or the linker can be introduced to the hyaluronic acid by forming amid group, hydrazide group, diacylhydrazide group, or carboxylic acid ester group. As for a hyaluronic acid derivative in which methacrylic anhydride or the linker is introduced to a hyaluronic acid by forming a carboxylic acid ester group, the methacrylic anhydride may be decomposed by hydrolysis in an administered solution or in vivo in a relatively short period of time. A linker including amid group or hydrazide group which is slowly hydrolyzed can be used to link methacrylic anhydride to the hyaluronic acid.

The dithiol-based crosslinker which reacts with the hyaluronic acid to which methacrylic anhydride is introduced through a linker can be a peptide having such a structure that a mercapto group (—SH)-containing cysteine is located at opposite ends and an arginin-glycine-aspartic acid sequence is interposed between the both ends. Each end of the crosslinker is bonded to a methacrylic anhydride-derived α,β-unsaturated carbonyl group of the hyaluronic acid derivative to form a hydrogel-type hyaluronic acid derivative.

Through the introduction of the peptide including an arginin-glycine-aspartic acid sequence, the adhesive force of the hyaluronic acid derivative with respect to a cell may be increased. Cell adhesion occurs by integrin that is a receptor existing at the surface of a cell in vivo and an adhesion protein existing in ECM, and in the adhesion protein, the arginin-glycine-aspartic acid sequence attaches a cell. Therefore, the cell adhesion can be effectively derived by introducing the dithiol-based crosslinker including the arginin-glycine-aspartic acid sequence to the hyaluronic acid derivative.

The matrix of the bone filling complex according to the current embodiment of the present invention described above may include a repeating unit represented by Formula 4.

Formula 2 where $R_1$ and $R_2$ can be respectively a hydrogen atom or $C_{1-6}$ alkyl group; $R_3$ is a single bond, —$(CH_2)x$—, —$CH_2$—$CH_2$—$(O$—$CH_2$—$CH_2)x$—, or —$NHCO$—$(CH_2)y$—$CONH$— where x is an integer of from 1 to 10 and y is an integer of from 0 to 10; C is cysteine; R denotes arginin; G denotes glycine; D denotes aspartic acid; and (—S—) denotes a sulfur derived from a mercapto group contained in cysteine. For example, each of $R_1$ and $R_2$ can be a hydrogen atom and $R_3$ can be —$NHCO$—$(CH_2)y$—$CONH$—.

The matrix is filled with the bone derivative. The matrix may have, for example, a network structure. In the network structure, the net is filled with the bone derivative. The bone derivative according to the current embodiment is substantially the same as the bone derivative of the bone filling complex according to the previous embodiment, and thus will not be described in detail.

A method of preparing the bone filling complex which has been described according to the current embodiment will now be described in detail.

Like the method of preparing the bone filling complex according to the previous embodiment, a carboxylic group of a hyaluronic acid is actively esterified, and then a linker including a functional group having reactivity with the active ester, such as a hydrazide group or an amino group, is introduced. At this time, the linker can be introduced to the carboxylic group of the hyaluronic acid in distilled water or a solution including at least one kind of an organic solvent. The organic solvent can be, for example, ethanol. The amount of the organic solvent may be about 60 vol % or less, and specifically about 50 vol %, based on the total amount of the entire solution.

Then, the bone derivative, for example, a calcium phosphate compound is dispersed to the hyaluronic acid solution to which the linker is introduced, and a dithiol crosslinker, for example, a peptide having such a structure that cysteine is located at opposite ends and an arginin-glycine-aspartic acid sequence is interposed between the both ends is added thereto. As a result, a bone filling complex in which the matrix having a network structure including the hydrogel-type hyaluronic acid derivative is filled with the bone derivative can be obtained by a Michael addition reaction. As described above, formation of the matrix and filling with the bone derivative can be performed substantially in-situ.

The bone filling complex is freeze-dried and formulated into various forms suitable for user's objectives. For example, the bone filling complex can be formulated into blocks, granules, or injectable forms.

The bone filling complex according to an embodiment of the present invention described above can be used as a dental bone filler. That is, an injured portion of an alveolar bone can be filled with the bone filling complex to derive regeneration of the alveolar bone.

The present invention will be described in further detail with reference to the following examples. These examples are for illustrative purposes only and are not intended to limit the scope of the present invention.

Experimental Example 1

Preparation of Bone Filling Complex

Experimental Example 1-1

Preparation of Hyaluronic Acid to which Hydrazide Group is Introduced

Three different hyaluronic acid solutions having a hyaluronic acid (Denkikagaku Kogyo Co. (Tokyo, Japan)) concentration of 2 mg/ml were prepared by respectively using distilled water, a mixture of distilled water and ethanol in a ratio of 75:25 vol %, and a mixture of distilled water and ethanol in a ratio of 50:50 vol %. Three more hyaluronic acid solutions having a hyaluronic acid (Denkikagaku Kogyo Co. (Tokyo, Japan)) concentration of 5 mg/ml were prepared in the same manner as with the 2 mg/ml concentration.

Then, a carboxylic group of the hyaluronic acid was activated using 1-ethyl-3-(3-dimethylaminopropyl) carbodiimide (EDC) (Sigma-Aldrich (St. Louis, Mo., USA)), and adipic acid dihydrazide (ADH)(Sigma-Aldrich (St. Louis, Mo., USA)) was added thereto and reacted together for about 2 hours at room temperature while the pH of the reaction solution was maintained to about 4.8 using 1N hydrochloric acid. At this time, the mole ratio of EDC to the carboxylic group was 4:1 and the mole ratio of ADH to the carboxylic group was 40:1.

The reaction product was dialyzed using 100 mM sodium chloride solution, 25% ethanol solution, and distilled water, and then the dialyzed product was freeze-dried. As a result, a hyaluronic acid (HA-ADH) to which a hydrazide group is added was obtained.

The introduction rate of the hydrazide group in each of the obtained hyaluronic acids was quantified using $^1$H-NMR (DPX300, Bruker, Germany). The results are shown in FIG. 1 (the cocentraiton of N-acetyl group (a) of the hyaluronic acid was about 2.1 ppm, and the concentration of methylene group (β, γ) of an adipic acid moiety was about 1.7 ppm, 1.8 ppm, 2.4 ppm, or 2.5 ppm).

Figure 1:
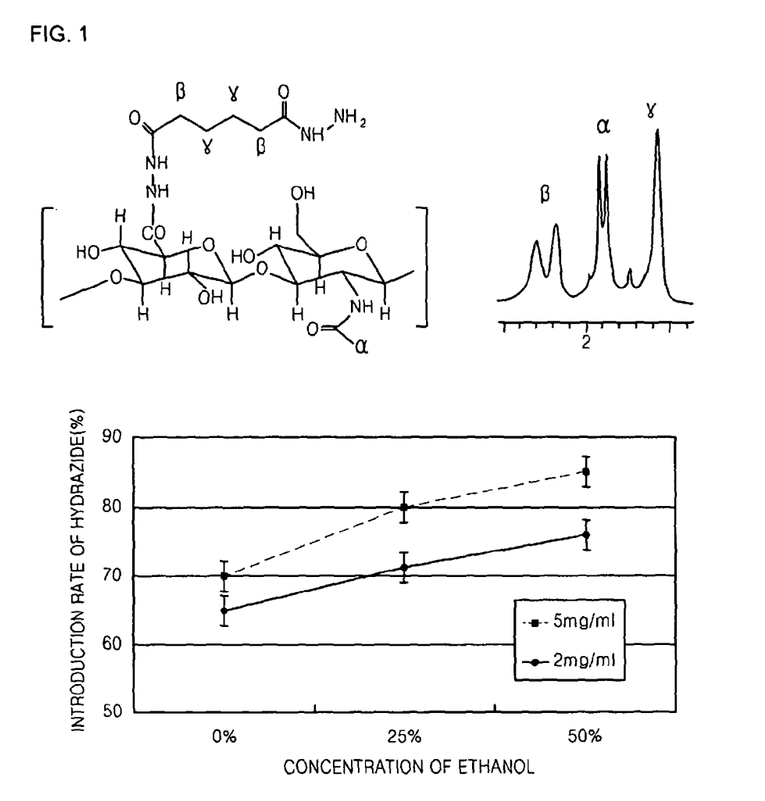
FIG. 1 is a graph showing a quantified introduction rate of a hydrazide group which is introduced to a hyaluronic acid measured through nuclear magnetic resonance (NMR).

Referring to FIG. 1, as the concentration of ethanol present in the hyaluronic acid solution is increased, the introduction rate of the hydrazide group increases.

Experimental Example 1-2

Quantification of Hyaluronic Acid to which Hydrazide Group is Introduced

Figure 2:
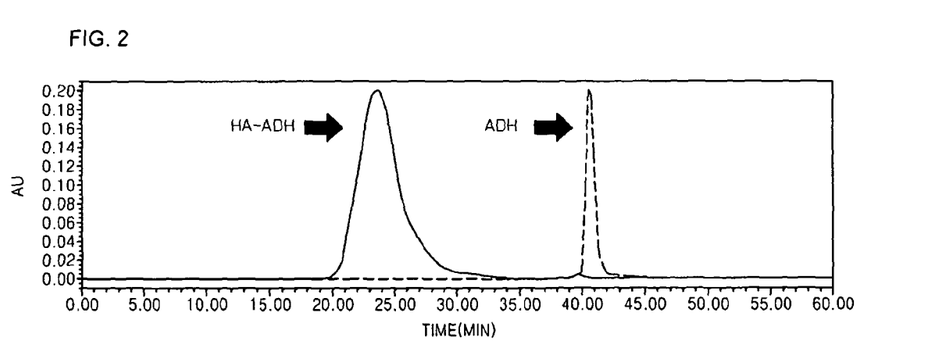
FIG. 2 is a graph showing results of high performance liquid chromatography (HPLS) of the dialysis product of a hyaluronic acid derivative to which a linker is introduced.

Among hyaluronic acids to which a hydrazide group is introduced prepared according to Experimental Example 1-1, the hyaluronic acid (HA-ADH) to which a hydrazide group is introduced prepared by having a hyaluronic acid concentration of 5 mg/ml prepared using a mixture of distilled water and ethanol in a ratio of 50:50 vol % was quantified using HPLC. The results are shown in FIG. 2.

The HPLC was performed using an 34 mM phosphate buffer (pH 6.6)/methanol=80:20 (v/v)) which acts as an eluate, a Waters 1525 binary HPLC pump, a Waters 2487 dual λ observance detector, a Waters 717 plus auto sampler (Milford, Mass., USA)), and ultrahydrogel 250 and 1000 columns (7.8 mm i.d.×30 cm) at a flow rate of 0.5 ml/min. At this time, the amount of the sample loaded was 10 μl and the concentration of the sample was 5 mg/ml. The detection wavelength was 210 nm.

Experimental Example 1-3

Durability Test of Hyaluronic Acid to which Hydrazide Group is Introduced Against Enzyme Each of about 4.57 mg/ml of a hyaluronic acid, about 4.57 mg/ml of a hyaluronic acid (HA-ADH) to which a hydrazide group is introduced in distilled water, and about 4.57 mg/ml of a hyaluronic acid (stealth HA-ADH) to which a hydrazide group is introduced in a solution including about 50 vol % of ethanol was dissolved in 1.8 ml 0.2M sodium phosphate buffer (pH 6.2). 200 μl of 15000 U/ml hyaluronidase (bovine testicular hyaluronidase) solution was added to each of the solution and incubated at about 37° C. for 48 hours.

An N-acetalhexosaminide bond of the hyaluronic acid and the hyaluronic acids (HA-ADH and stealth HA-ADH) to which a hydrazide group is introduced was decomposed by a hyaluronidase as illustrated in Reaction Scheme 1.

Reaction Scheme 1

After the hyaluronic acid and the hyaluronic acids (HA-ADH and stealth HA-ADH) to which a hydrazide group is introduced were treated with the hyaluronidase, a double bond in the decomposition products was quantified by ultraviolet spectroscopy and the decomposition speeds were measured by GPC analysis. The results are shown in FIG. 3.

Figure 3:
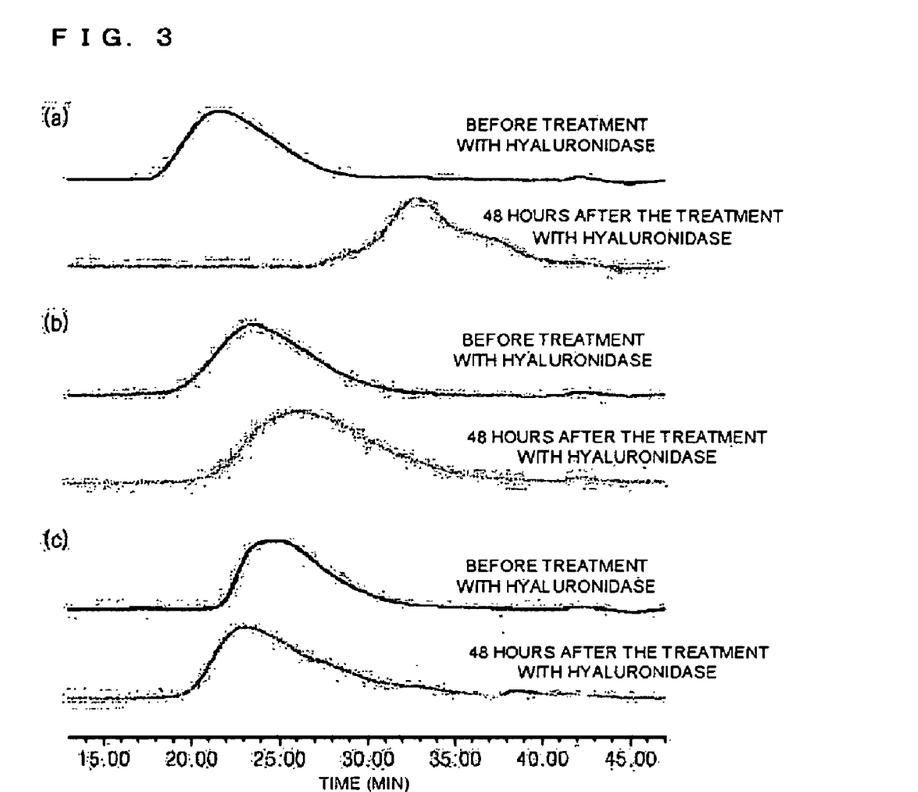
FIG. 3 is a graph showing results of gel permeation chromatography (GPC) of the decomposition products of a hyaluronic acid and hyaluronic acid derivatives to which a linker is introduced which are treated with a hyaluronidase.

Referring to FIG. 3, GPC analysis results before and after a hyaluronic acid was treated with the hyaluronidase are shown in (a); GPC analysis results before and after a hyaluronic acid (HA-ADH) to which a hydrazide group is introduced in distilled water was treated with the hyaluronidase are shown in (b); and GPC analysis results before and after a hyaluronic acid (stealth HA-ADH) to which a hydrazide group is introduced in a solution including about 50 vol % of ethanol was treated with the hyaluronidase are shown in (c).

In GPC, a peak of a material having a large molecular weight occurs first before a material having a small molecular weight occurs. Accordingly, a peak of the decomposition product obtained by performing a decomposition reaction using an enzyme occurs late because the molecular weight of the decomposition product is decreased. In consideration of the same period of time after the enzyme treatment, as the peak is more shifted, more decomposition occurs. In (a), (b) and (c), the concentration of the hyaluronic acid was about 5 mg/ml, and in (b) and (c), the introduction rate of the hydrazide groups was 70.47% and 82.82%, respectively.

As illustrated in FIG. 3, as the introduction rate of the hydrazide group which is introduced to the hyaluronic acid is higher, less hyaluronic acid is decomposed by the enzyme.

Experimental Example 1-4

Durability Test of Hydrogel-Type Hyaluronic Acid Derivative

Each of 12 mg of a hyaluronic acid having an introduction rate of the hydrazide group of 69.39 mole %, 12 mg of a hyaluronic acid having an introduction rate of the hydrazide group of 79.61 mole %, and 12 mg of a hyaluronic acid having an introduction rate of the hydrazide group of 84.98 mole % was completely dissolved in 270 μl of PBS (0.01M, pH7.4, 25° C.). Then, 180 μg of each solution was loaded to a syringe having its front part cut.

Bis(sulfosuccinimidyl)suberate was dissolved in 20 μl of PBS. Then, the mixture was added to the hyaluronic acid solution contained in the syringe and then homogeneously mixed. The amount of the bis(sulfosuccinimidyl)suberate added was 20 mole % of ADH which was introduced to the hyaluronic acid.

The obtained precursor solution was incubated at 37° C. for one hour and a crosslinking reaction was completed.

Each of the complete hydrogel-type hyaluronic acids (about 200 μl) was added to a 4 ml vial. 0.9 ml of 0.2M sodium phosphate buffer (pH 6.2) was added to each vial. 0.9 ml of hyaluronate lyase 180U-containing 0.2M sodium phosphate buffer (pH 6.2) was added to each vial. These vials were incubated at 37° C. for 96 hours.

At an every sampling time, 200 μl of a supernatant was extracted from each vial and 200 μl of 0.2M sodium phosphate buffer (pH 6.2) was added to the vial. The dilution of the supernatant occurring at every sampling time was compensated later. 200 μl of each extracted supernatant was immersed in a vessel containing a boiling water for about 3 minutes to stop the activity of the enzyme.

Figure 4:
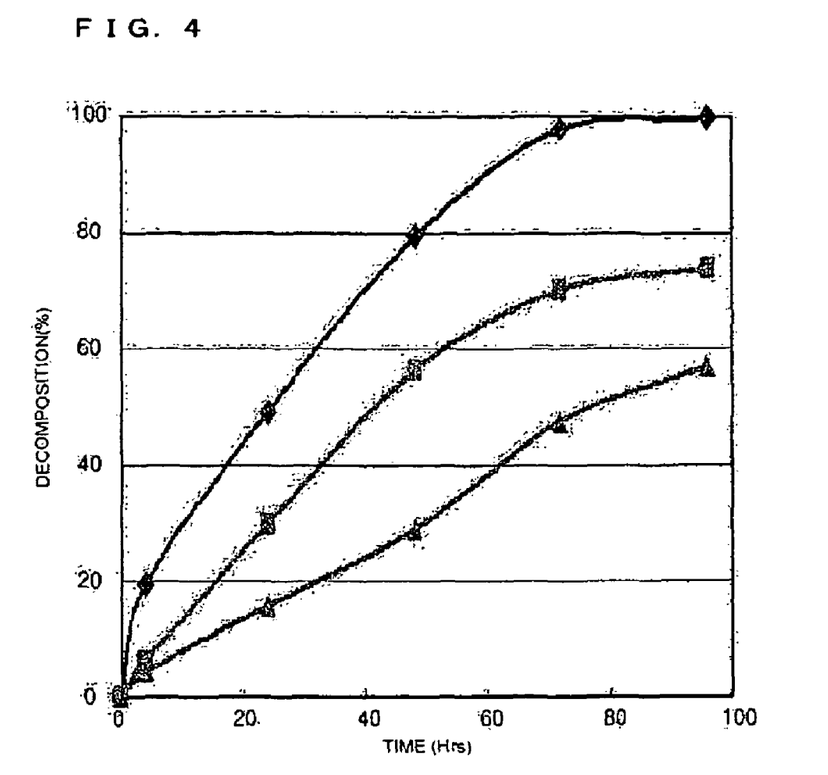
FIGS. 4 and 5 are graphs showing results of the carbazole assay and GPC of decomposition products of hydrogel-type hyaluronic acid derivatives which are treated with a hyaluronidase, respectively.
Figure 5:
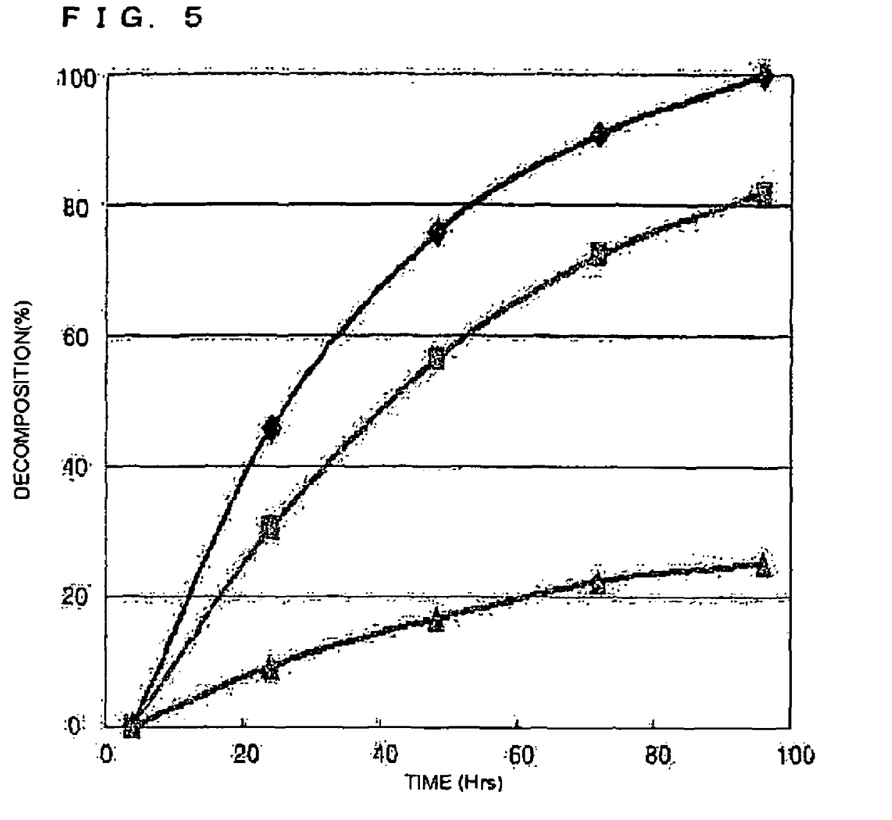

The decomposition of the hydrogel-type hyaluronic acid derivative by the hyaluronidase was identified by measuring the amount of a glucuronic acid which was decomposed to be included in the supernatant through a carbazole assay and GPC. The results of the carbazole assay are shown in FIG. 4, and the results of GPC are shown in FIG. 5. According to a carbazole assay, a degree of decomposition of the hyaluronic acid can be quantified by measuring an absorbance of a sample in which a color reaction occurs using a UV spectrophotometer.

Referring to FIGS. 4 and 5, it can be seen that the hyaluronic acid derivative (♦) having an introduction rate of the hydrazide group of 69.39 mole %, the hyaluronidase than the hyaluronic acid derivative (■) having an introduction rate of the hydrazide group of 79.61 mole %, the hyaluronidase than the hyaluronic acid derivative (▲) having an introduction rate of the hydrazide group of 84.98 mole % are decomposed at various speeds. That is, as an introduction rate of the hydrazide group is greater, the decomposition occurs more slowly. In other words, an introduction rate of the hydrazide group is greater, the decomposition of the hyaluronic acid derivative by the decomposition enzyme is more hindered.

Experimental Example 1-5

Preparation of Bone Filling Complex Including Matrix and Bone Derivative Filling the Matrix 12 mg of hyaluronic acid having an introduction rate of a hydrazide group of 69.39 mole % was completely dissolved in 270 μl of PBS (0.01M, pH7.4, 25° C.). Then, 180 μg of the solution was loaded to a syringe having its front portion cut. 100 mg/ml of hydroxyapatite (Sigma-Aldrich (St. Louis, Mo., USA)) based on the final hydrogel amount of 200 μl was added to the hyaluronic acid (HA-ADH) solution to which a hydrazide group is introduced, and mixed together to obtain a homogeneous solution. bis(sulfosuccinimmidyl)suberate was dissolved in 20 μl of PBS and then added to the hyaluronic acid solution contained in the syringe and homogeneously mixed together. The amount of the bis(sulfosuccinimmidyl)suberate added was 20 mole % of ADH which is introduced to the hyaluronic acid. The obtained precursor solution was incubated at 37° C. for one hour and a crosslinking reaction was completed. As a result, a bone filling complex including a matrix having a network structure including a hydrogel-type hyaluronic acid derivative and a bone derivative filling the matrix was completely prepared.

The bone filling complex was quickly froze in a deep freezer at about −70° C., and then loaded to a freeze dryer while a low temperature was maintained in vacuum to remove moisture from the matrix. The resultant product was pressed to formulate in blocks.

Experimental Example 2

Preparation of Bone Filling Complex

Experimental Example 2-1

Preparation of Hyaluronic Acid to which Methacrylic Anhydride is Introduced 50 mg of hyaluronic acid (HA-ADH) having an introduction ratio of a hydrazide group of 72.89 mole % was dissolved in 2.25 ml of distilled water, and then 0.25 ml of a phosphate buffer (200 mM, pH 8.0) was added thereto to control the pH to 8. A methacrylic anhydride (MW=154.17) having such an amount that the ratio of methacrylic anhydride to the hydrazide group is 20:1 was added to a hyaluronic acid (HA-ADH) solution to which a hydrazide group is introduced.

The resultant solution was stirred for 4 hours at room temperature, and then precipitated using ethanol to obtain a hyaluronic acid derivative (HA-MA). The obtained hyaluronic acid derivative (HA-MA) was washed using ethanol three times and dried at room temperature.

The introduction rate of methacrylic anhydride with respect to the hyaluronic acid was obtained through $^1$H NMR analysis.

Experimental Example 2-2

Preparation of the Hyaluronic Acid into Hydrogel-Type Hyaluronic Acid Derivative 11 mg of hyaluronic acid (HA-MA) prepared according to Experimental Example 2-1 was dissolved in 16 μl/ml of PBS (240 ul, 10 mM, pH7.4) including TEA for two hours. When TEA is added to PBS, the pH is changed to 9.5. 100 mg/ml of hydroxyapatite (Sigma-Aldrich (St. Louis, Mo., USA)) based on the final hydrogel amount of 250 μl was added to the hyaluronic acid (HA-MA) solution to which a methacrylic anhydride is introduced and mixed together to obtain a homogeneous solution. A peptide including cysteine-arginin-glycine-aspartic acid-arginin-cysteine in which a mole ratio of a thiol to a methacrylic anhydride is 1:2 that is a crosslinker was dissolved in 10 μl of DMSO. Then, the resultant solution was added to the hyaluronic acid derivative (HA-MA) solution and immediately vortexed to generate a whirlpool until a homogeneous solution was obtained.

250 μl of the obtained precursor solution was loaded to a syringe having its front part cut and incubated at 37° C. until the crosslinking reaction was complete. As a result, a bone filling complex including a matrix having a network structure having a hydrogel-type hyaluronic acid derivative and a bone derivative filling the matrix was obtained.

The bone filling complex was quickly froze in a deep freezer at about −70° C., and then loaded to a freeze dryer while a low temperature was maintained in vacuum to remove moisture from the matrix. The resultant product was pressed to formulate in blocks.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

A bone filling complex according to the present invention includes a matrix including a hyaluronic acid derivative and a bone alternative which fills the matrix, and thus adhesion can be prevented and excellent bone generation property can be obtained. For example, the bone filling complex can be used to an injured portion of an alveolar bone to derive regeneration of the alveolar bone.

The invention claimed is:

1. A bone filling complex comprising:
a matrix comprising a hydrogel-type hyaluronic acid derivative, wherein the hydrogel-type hyaluronic acid derivative is obtained by reacting a hyaluronic acid with a bis(sulfosuccinimmidyl)suberate or a dithiol-based crosslinker, wherein the dithiol-based derivative is a peptide which has cysteine at its opposite ends and an arginine-glycine-aspartic acid sequence interposed between the ends; and
a bone derivative, wherein the bone derivative is a calcium phosphate-based compound, filling the matrix.

2. The bone filling complex of claim 1, wherein the hydrogel-type hyaluronic acid derivative is obtained by reacting a hyaluronic acid with the bis(sulfosuccinimmidyl)suberate.

3. The bone filling complex of claim 2, wherein the suberate is bonded to a carbonyl group of the hyaluronic acid through a linker.

4. The bone filling complex of claim 3, wherein the linker comprises at least two amino groups, wherein one amino group of the amino groups is bonded to the carboxylic group of the hyaluronic acid and another amino group of the amino groups is bonded to a carbonyl group of the suberate.

5. The bone filling complex of claim 4, wherein the matrix comprises at least one unit represented by Formula 1:

Formula 1 where $R_1$ and $R_2$ can be respectively a hydrogen atom or $C_{1-6}$ alkyl group; and $R_3$ is a single bond, —(CH$_2$)x-, —CH$_2$—CH$_2$—(O—CH$_2$—CH$_2$)x-, or —NHCO—(CH$_2$)y-CONH— where x is an integer of from 1 to 10 and y is an integer of from 0 to 10.

6. The bone filling complex of claim 5, wherein each of $R_1$ and $R_2$ is hydrogen atom and $R_3$ is —NHCO—(CH$_2$)y-CONH—.

7. The bone filling complex of claim 1, wherein the hydrogel-type hyaluronic acid derivative is obtained by reacting a hyaluronic acid to which a methacrylic anhydride is introduced with a dithiol-based crosslinker, wherein the dithiol-based crosslinker is a peptide which has cysteine at its opposite ends and an arginine-glycine-aspartic acid sequence interposed between the ends.

8. The bone filling complex of claim 7, wherein the methacrylic anhydride is bonded to a carboxylic group of the hyaluronic acid through a linker.

9. The bone filling complex of claim 8, wherein the linker comprises at least two amino groups, wherein one amino group of the amino groups is bonded to the carboxylic group of the hyaluronic acid and another amino group of the amino groups is bonded to a carbonyl group of the methacrylic anhydride.

10. The bone filling complex of claim 7, wherein the matrix comprises at least one unit represented by Formula 2:

Formula 2 where $R_1$ and $R_2$ can be respectively a hydrogen atom or $C_{1-6}$ alkyl group; $R_3$ is a single bond, —(CH$_2$)x-, —CH$_2$—CH$_2$—(O—CH$_2$—CH$_2$)x-, or —NHCO—(CH$_2$)y-CONH— where x is an integer of from 1 to 10 and y is an integer of from 0 to 10; C is cysteine; R denotes arginin; G denotes, glycine; D denotes aspartic acid; and (—S—) denotes a sulfur derived from a mercapto group contained in cysteine.

11. The bone filling complex of claim 10, wherein each of $R_1$ and $R_2$ is hydrogen atom and $R_3$ is —NHCO—$(CH_2)$y-CONH—.

12. The bone filling complex of claim 1, wherein the matrix has a network structure.

13. The bone filling complex of claim 1, wherein the bone filling complex is formulated into blocks, granules, or an injectable form.

14. A method of preparing a bone filling complex, the method comprising:

forming a matrix comprising a hydrogel-type hyaluronic acid derivative, wherein the forming of a matrix comprises reacting a hyaluronic acid with a bis(sulfosuccinimidyl)suberate or a dithiol-based crosslinker, wherein the dithiol-based crosslinker is a peptide which has cysteine at its opposite ends and an arginine-glycine-aspartic acid sequence interposed between the ends; and filling the matrix with a bone derivative, wherein the bone derivative is a calcium phosphate-based compound.

15. The method of claim 14, wherein the forming of a matrix comprises reacting a hyaluronic acid with the bis(sulfosuccinimmidyl)suberate.

16. The method of claim 15, wherein the suberate is bonded to a carbonyl group of the hyaluronic acid through a linker.

17. The method of claim 16, wherein the linker comprises at least two amino groups, wherein one amino group of the amino groups is bonded to the carboxylic group of the hyaluronic acid and another amino group of the amino groups is bonded to a carbonyl group of the suberate.

18. The method of claim 17, wherein the matrix comprises at least one unit represented by Formula 1:

where $R_1$ and $R_2$ can be respectively a hydrogen atom or $C_{1-6}$ alkyl group; and $R_3$ is a single bond, —$(CH_2)$x-, —$CH_2$—$CH_2$—(O—$CH_2$—$CH_2$)x-, or —NHCO—$(CH_2)$y-CONH— where x is an integer of from 1 to 10 and y is an integer of from 0 to 10.

19. The method of claim 18, wherein each of $R_1$ and $R_2$ is hydrogen atom and $R_3$ is —NHCO—$(CH_2)$y-CONH—.

20. The method of claim 16, wherein the linker is bonded to the carboxylic group of the hyaluronic acid in a solution comprising at least one organic solvent in an amount ranging from 0 to 60 vol %.

21. The method of claim 20, wherein the organic solvent is ethanol.

22. The method of claim 14, wherein the forming of the matrix further comprises:

introducing methacrylic anhydride to a hyaluronic acid; and reacting the hyaluronic acid to which the methacrylic anhydride is introduced with a dithiol-based crosslinker, wherein the dithiol-based crosslinker is a peptide which has cysteine at its opposite ends and an arginine-glycine-aspartic acid sequence interposed between the ends.

23. The method of claim 22, wherein the methacrylic anhydride is bonded to a carboxylic group of the hyaluronic acid through a linker.

24. The method of claim 23, wherein the linker comprises at least two amino groups, wherein one amino group of the amino groups is bonded to the carboxylic group of the hyaluronic acid and another amino group of the amino groups is bonded to a carbonyl group of the methacrylic anhydride.

25. The method of claim 22, wherein the matrix comprises at least one unit represented by Formula 2:

Formula 1

Formula 2 where $R_1$ and $R_2$ can be respectively a hydrogen atom or $C_{1-6}$ alkyl group; $R_3$ is a single bond, —$(CH_2)x$-, —$CH_2$—$CH_2$—(O—$CH_2$—$CH_2$)x-, or —NHCO—$(CH_2)y$-CONH— where x is an integer of from 1 to 10 and y is an integer of from 0 to 10; C is cysteine; R denotes arginin; G denotes glycine; D denotes aspartic acid; and (—S—) denotes a sulfur derived from a mercapto group contained in cysteine.

26. The method of claim 25, wherein each of $R_1$ and $R_2$ is hydrogen atom and $R_3$ is —NHCO—$(CH_2)y$-CONH—.

27. The method of claim 23, wherein the linker is bonded to the carboxylic group of the hyaluronic acid in a solution comprising at least one organic solvent in an amount ranging from 0 to 60 vol %.

28. The method of claim 27, wherein the organic solvent is ethanol.

29. The method of claim 14, wherein the forming of the matrix and the filling with the bone derivative are performed substantially in situ.

* * * * *